United States Patent
Ong et al.

(10) Patent No.: US 9,675,501 B2
(45) Date of Patent: Jun. 13, 2017

(54) ABSORBENT ARTICLE INCLUDING SUPERABSORBENT YARN

(71) Applicant: Kimberly-Clark Worldwide, Inc., Neenah, WI (US)

(72) Inventors: YeinSze Ong, Singapore (SG); Franz Aschenbrenner, Kastl (DE); DooHong Kim, Seoul (KR); Meijia Ng, SeongNam-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 425 days.

(21) Appl. No.: 13/716,912

(22) Filed: Dec. 17, 2012

(65) Prior Publication Data

US 2013/0158494 A1 Jun. 20, 2013

Related U.S. Application Data

(60) Provisional application No. 61/577,403, filed on Dec. 19, 2011.

(51) Int. Cl.
*A61F 13/538* (2006.01)
*A61F 13/53* (2006.01)

(52) U.S. Cl.
CPC .. *A61F 13/53* (2013.01); *A61F 2013/530481* (2013.01); *A61F 2013/530613* (2013.01); *A61F 2013/530992* (2013.01)

(58) Field of Classification Search
CPC .......... A61F 13/53; A61F 2013/530481; A61F 2013/530613; A61F 2013/530664; A61F 2013/530992; A61F 2013/5355; A61F 2013/49486; A61F 13/49473
USPC ....... 604/364–368, 370, 374, 375, 372, 384; 442/2, 63, 118, 152, 153, 218, 170, 241, 442/318
See application file for complete search history.

(56) References Cited

U.S. PATENT DOCUMENTS

| 4,235,237 A | 11/1980 | Butterworth et al. |
| 4,318,408 A | 3/1982 | Korpman |

(Continued)

FOREIGN PATENT DOCUMENTS

| EP | 0 425 269 A2 | 5/1991 |
| JP | 2001-329439 A | 11/2001 |
| WO | WO2006126233 A1 * | 11/2006 |

*Primary Examiner* — Paula L Craig
(74) *Attorney, Agent, or Firm* — Kimberly-Clark Worldwide, Inc.

(57) ABSTRACT

The present invention discloses and claims an absorbent article which utilizes an absorbent portion that includes superabsorbent yarn as part of the absorbent portion, such that liquid is wicked to the perimeter or select regions of the absorbent portion, or the perimeter of the absorbent article itself, taking full advantage of either the depth, width, length or combination of dimensions of the absorbent portion, or absorbent article. The superabsorbent yarn can be one or more of several types, including encapsulated yarn, multi-layered encapsulated yarn, coated yarn and sliver-formed yarn as long as such yarn includes at least two components, those being a superabsorbent polymer and a second material which promotes distribution of liquid along the yarn length. In alternatives of the invention, such absorbent article utilizing the superabsorbent yarn provides passive visual signals to consumers, of article saturation levels prior to leakage.

13 Claims, 10 Drawing Sheets

(56) References Cited

U.S. PATENT DOCUMENTS

| | | | |
|---|---|---|---|
| 4,340,058 A * | 7/1982 | Pierce | A61F 13/47218 604/372 |
| 4,361,151 A * | 11/1982 | Fitzgerald | A61F 13/2062 604/15 |
| 4,418,524 A | 12/1983 | Ito et al. | |
| 4,490,147 A * | 12/1984 | Pierce | A61F 13/47218 604/378 |
| 4,524,577 A | 6/1985 | Ito et al. | |
| 4,809,493 A | 3/1989 | Genba et al. | |
| 5,207,662 A * | 5/1993 | James | A61F 13/15211 604/364 |
| 5,451,219 A * | 9/1995 | Suzuki | A61F 13/515 604/358 |
| H1565 H | 7/1996 | Brodof et al. | |
| 5,534,304 A * | 7/1996 | Geursen | D06M 15/263 427/121 |
| H1585 H * | 8/1996 | Ahr | A61F 13/53713 604/378 |
| 5,599,337 A * | 2/1997 | Mccoy | A61F 13/47227 604/367 |
| 5,643,238 A * | 7/1997 | Baker | A61F 13/5323 156/276 |
| 5,653,843 A * | 8/1997 | Fell | A61F 13/4942 156/164 |
| 5,662,634 A * | 9/1997 | Yamamoto | A61F 13/5323 156/229 |
| 5,695,487 A * | 12/1997 | Cohen | A61F 13/538 604/378 |
| 5,869,596 A | 2/1999 | Ahmed et al. | |
| 5,941,863 A * | 8/1999 | Guidotti | A61F 13/535 604/358 |
| 6,245,961 B1 * | 6/2001 | Roxendal | A61F 13/53713 604/367 |
| 6,342,298 B1 * | 1/2002 | Evans | A61F 13/53 428/370 |
| 6,448,466 B1 * | 9/2002 | Ribeiro de Carvalho | A61F 13/47227 604/354 |
| 6,458,456 B1 | 10/2002 | Zainiev et al. | |
| 6,497,955 B1 * | 12/2002 | Phillips | A61F 13/532 428/375 |
| 6,521,431 B1 | 2/2003 | Kiser et al. | |
| 6,576,338 B1 | 6/2003 | Meijer et al. | |
| 6,605,751 B1 * | 8/2003 | Gibbins | A61K 9/70 602/41 |
| 6,648,865 B1 * | 11/2003 | Stiehl | A61F 13/495 428/196 |
| 6,696,618 B2 | 2/2004 | Dodge, II et al. | |
| 6,808,801 B2 | 10/2004 | George et al. | |
| 7,045,673 B1 | 5/2006 | Batich et al. | |
| 7,575,573 B1 * | 8/2009 | Roe | A61F 13/49011 604/385.27 |
| 7,638,445 B2 | 12/2009 | Patrick | |
| 2002/0029023 A1 * | 3/2002 | Furuya | A61F 13/513 604/368 |
| 2002/0034907 A1 | 3/2002 | Groitzsch et al. | |
| 2002/0035352 A1 * | 3/2002 | Ronnberg | A61F 13/511 604/366 |
| 2002/0173762 A1 | 11/2002 | Ishikawa et al. | |
| 2003/0065299 A1 * | 4/2003 | Carlucci et al. | 604/385.01 |
| 2003/0088229 A1 | 5/2003 | Baker et al. | |
| 2005/0008776 A1 * | 1/2005 | Chhabra | A61F 13/15577 427/180 |
| 2005/0130540 A1 | 6/2005 | Crane | |
| 2005/0143703 A1 | 6/2005 | Persson | |
| 2005/0165376 A1 | 7/2005 | Buchholz et al. | |
| 2005/0256482 A1 * | 11/2005 | Minoguchi | A61F 13/2051 604/385.17 |
| 2008/0255531 A1 | 10/2008 | Ring et al. | |
| 2008/0262451 A1 | 10/2008 | Broden | |
| 2009/0054860 A1 | 2/2009 | Young et al. | |
| 2009/0176422 A1 | 7/2009 | Patrick | |
| 2009/0312729 A1 | 12/2009 | Roche et al. | |
| 2010/0003517 A1 * | 1/2010 | Hansson | A61F 13/53 428/373 |
| 2010/0042034 A1 | 2/2010 | Riesinger et al. | |

* cited by examiner

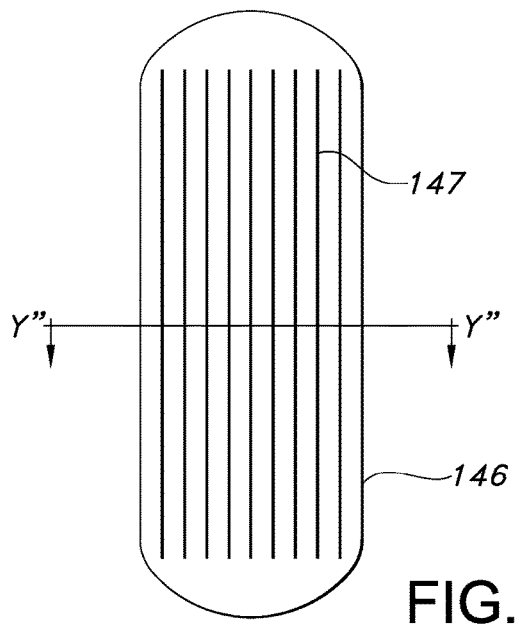
FIG. 12
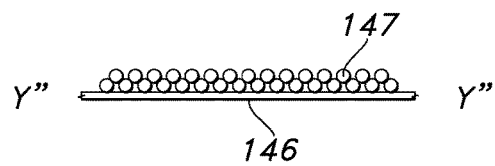
FIG. 13A
FIG. 13B
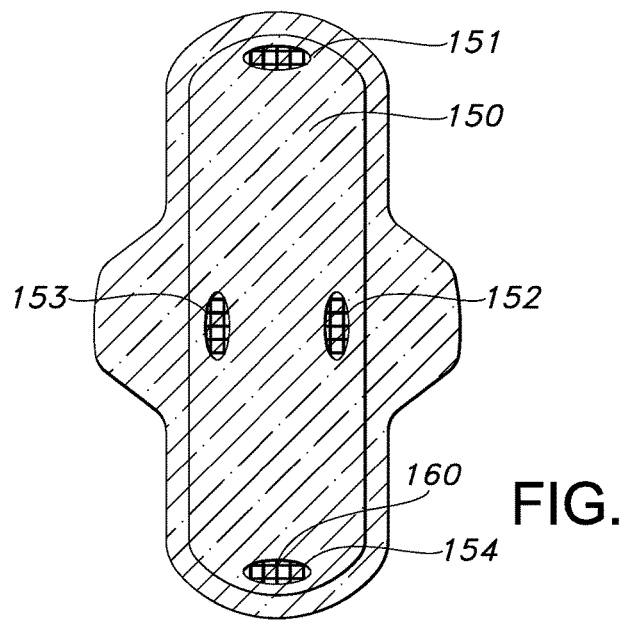
FIG. 14

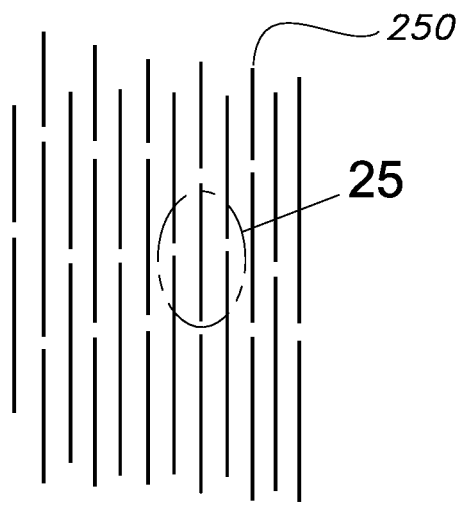
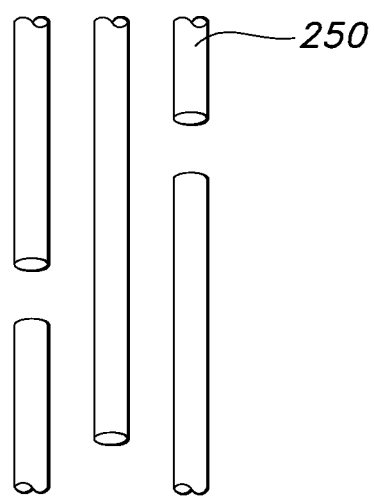
FIG. 24        FIG. 25
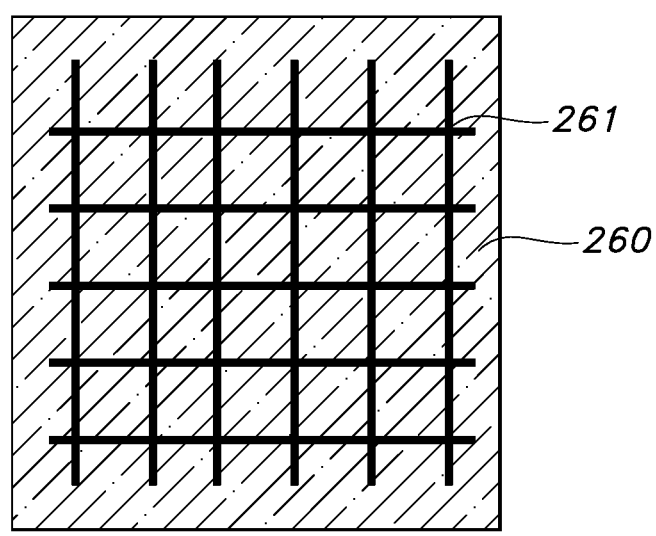
FIG. 26

ABSORBENT ARTICLE INCLUDING SUPERABSORBENT YARN

PRIORITY

This non-provisional application claims priority of Provisional Application No. 61/577,403, filed on Dec. 19, 2011. The entirety of Application No. 61/577,403 is incorporated herein by reference.

FIELD OF THE INVENTION

The present invention is generally directed to absorbent personal care articles. In particular, the present invention is directed to absorbent portions of personal care articles which assist in absorbing and wicking fluids across various dimensions of the articles.

BACKGROUND OF THE INVENTION

The present invention is directed to absorbent articles and in particular, personal care absorbent articles utilized to collect and retain body fluids, liquids, or exudates including, but not limited to urine, feces, menses, and wound-released fluids, such as blood or pus. In the context of such products, comfort and absorbency are two main attributes and areas of concern for the wearer. This is particularly true with child care, adult care and feminine care products such as diapers, incontinence articles, feminine hygienic pads, liners and tampons. Less so with wound care articles, paper towels and wipes, but similar needs exist for bandage materials.

In the personal care area, large portions of the absorbent capacity of absorbent articles have often been free of soiling at the time of product disposal, thereby depriving consumers of the full value of these products. Such inefficient usage of a product is often visually apparent to a user as fluid staining occurs in only a limited area on the product. Such inefficient usage of a product may lead to consumer frustration, as a consumer may infer that the product failed to capture much waste, led to a leak, or at a minimum, did not provide sufficient value to justify the expense. Therefore, in the personal care area, numerous absorbent structures have been developed for efficiently utilizing larger areas of the absorbent portion of the articles. For example, multiple absorbent layered structures have been employed in articles (one layer stacked over another) to help transfer liquid or distribute liquid to larger areas of absorbent layers positioned beneath a liquid entry layer. However, in such layers, if structures with improperly matched capillary features or improperly placed superabsorbents are used, liquid may have a tendency to be blocked in movement in one or more directions, such as through gel blocking (for superabsorbent sheets) or misaligned capillary action, within density-gradient, layered structures. If such absorbent materials are not efficiently used, large areas of the absorbent article are devoid of waste at the time of article disposal, thereby failing to take advantage of the potential overall absorbent capacity of the article.

Despite various designs in the absorbent art, there is still a need for an absorbent article/product which when worn, takes full advantage of an absorbent structure to reduce leakage, and which is relatively thin and flexible for ease of wear in a consumer's undergarments. Such a thin and flexible product would also provide relative discreteness, an attribute that is also desired by consumers.

Even when article absorbent cores are functioning, such cores have a propensity to leak at certain locations on a product (depending on product type and user habits). Such leakage may cause frustrating and embarrassing staining of a user's under or even outergarments. While various systems have been developed to signal a user of an impending leak or saturation of an absorbent article, such signals are often conveyed using chemical or physical communications such as temperature change, scent change, print change upon product saturation or alternatively, embossment marker features. In such "signal" products, additional costly chemistries are needed to convey the message to the user, or alternatively, the user may have to remove the product, step off of the product, or out of the product, to see the signal. It therefore is desirable that "signal" products be developed by which a user could casually observe without use of additional chemistry (such as for example traditional "wetness indicator" technology), or product removal or special movements, so as to view a signal of impending leakage. There is also a need for feminine hygiene articles that allow a consumer the ability to see that such products are working throughout their lifecycle, so as to afford a sense of security and emotional comfort to the consumer.

Braided absorbent yarn-like materials have been used in connection with personal care articles, and such have been known to include superabsorbent polymers. However, use of such braided materials has been limited to specific projection-like structures for capturing moisture from crevices associated with a user's body. Such braided structures can for example, be seen in US20090312729 to Roche del Ayala and are positioned outside the main body of a personal care absorbent article.

Absorbent yarn materials have been described for use in personal care articles in conjunction with traditional absorbent sheets for retention of fluids. Such for example may be found in US20030088229 to Baker. However, such reference does not describe the use of superabsorbent yarns in-and-of themselves, as the sole basis of absorbent cores/portions of absorbent cores. Further, such reference relies on spatial channels between yarns to move fluid to the periphery of absorbent core structures.

Superabsorbent containing spun filaments (as opposed to yarn) in which superabsorbent is encapsulated by fluid permeable material, have been taught and suggested for use in personal care products. Such for example was disclosed in US20050130540 to Crane. While such filaments have been suggested for use in absorbent cores of personal care products, the use of such filaments have been described in sheet-like layers, which utilize large amounts of material in a non-targeted/inefficient fashion. Transport of such absorbent sheets is often cumbersome.

Absorbent sheets may also be stiff and subsequently add stiffness to the absorbent product. Such usage may be wasteful and expensive, and may impact a product's bulk, flexibility, and breathability, physical attributes that are of particular sensitivity to the women who use feminine hygiene products. In this regard, see also U.S. Pat. No. 6,458,456 to Zainiev and US20090054860 to Young et al.

It would be desirable to develop an absorbent article or an absorbent portion of an absorbent article that was flexible in use, that made efficient use of peripheral areas of the absorbent portion and which provided a signal or communication to the consumer of level of usage or saturation. In some absorbent articles it would be desirable to control flow of absorbed fluids to certain areas of an absorbent article, such as away from the transverse direction of an article, and in the longitudinal direction of the absorbent article. It is also desirable to have an absorbent article that could block or slow the flow of fluids to traditionally high risk leakage areas, such as in the wing or flap regions of child care products and feminine care hygienic pads/sanitary napkins.

SUMMARY OF THE INVENTION

Objects and advantages of the invention are set forth below in the following description, or may be learned through practice of the invention. In one embodiment of the invention, an absorbent article has a longitudinal and transverse direction, and includes a fluid permeable topsheet, a fluid impermeable backsheet, an absorbent portion positioned between the topsheet and the backsheet, characterized in that the absorbent portion includes at least superabsorbent yarn including superabsorbent and fluid permeable components. The fluid permeable components are for either distributing fluid along the yarn length, alternatively for retaining fluid, or for accomplishing both functions.

In an alternative embodiment of the invention, an absorbent article includes an absorbent portion that includes solely superabsorbent yarn. In a further alternative embodiment of the invention, an absorbent article includes an absorbent portion that further includes solely superabsorbent yarn and a carrier sheet. In a further alternative embodiment of the invention, an absorbent article includes an absorbent portion having superabsorbent yarn which is selected from encapsulated superabsorbent yarn, multi-layered encapsulated superabsorbent yarn, coated superabsorbent yarn, superabsorbent yarn made from superabsorbent containing fibers or filaments, and sliver-formed superabsorbent yarn. In a further alternative embodiment of the invention, an absorbent article includes an absorbent portion having a superabsorbent yarn that is a multi-layered encapsulated superabsorbent yarn. In a further alternative embodiment of the invention, an absorbent article includes an absorbent portion with a multilayered encapsulated superabsorbent yarn, which yarn includes a topsheet layer and at least two other layers. In a further alternative embodiment of the invention, the absorbent article includes an absorbent portion with superabsorbent yarn and an additional absorbent layer. In still a further alternative embodiment of the invention, the absorbent article with superabsorbent yarn includes a shaping layer. In still a further alternative embodiment of the invention, the absorbent article with superabsorbent yarn in the absorbent portion includes an additional layer between a topsheet and an absorbent portion.

In still a further alternative embodiment of the invention an additional layer between the absorbent portion containing superabsorbent yarn and the topsheet defines one or more openings through which the superabsorbent yarn is visible through the topsheet. In a further alternative embodiment of the invention, the topsheet is translucent to allow the viewing of the superabsorbent yarn through the topsheet. In still a further alternative embodiment of the invention, the absorbent article containing the superabsorbent yarn is either a feminine hygiene article, an adult incontinence article, a baby or child care article, a bandage, or a wiping towel. In a further alternative embodiment of the invention, in the absorbent article containing superabsorbent yarn, the superabsorbent yarn is arranged in a superabsorbent portion as free superabsorbent yarn strands. In a further alternative embodiment of the invention, in the absorbent article containing superabsorbent yarn, the superabsorbent yarn is arranged in a superabsorbent portion as a matrix. In a further alternative embodiment of the invention, in the absorbent article containing superabsorbent yarn, the superabsorbent yarn is arranged along peripheral edges of the article. In a further alternative embodiment of the invention, in the absorbent article containing superabsorbent yarn, the superabsorbent yarn is arranged adjacent other strand materials. In still a further alternative embodiment of the invention, the superabsorbent yarn is arranged such that an absorbent portion includes different strand densities of superabsorbent yarn per unit area, along the absorbent portion. In a further alternative embodiment of the invention, in the absorbent article containing superabsorbent yarn, the superabsorbent yarn is arranged on the article in a location separate from said absorbent portion. In a further alternative embodiment of the invention, in the absorbent article containing superabsorbent yarn, the superabsorbent yarn is severed into multiple pieces along at least one direction of said article.

In a further alternative embodiment of the invention, an absorbent article has a longitudinal and transverse direction, and includes an absorbent portion consisting essentially of superabsorbent yarn including superabsorbent and fluid permeable components with the fluid permeable components for either distributing fluid within the yarn length or alternatively for retaining fluid. In still a further alternative embodiment, such an absorbent article includes encapsulated superabsorbent yarn. In still a further alternative embodiment, such superabsorbent yarn includes multi-layered encapsulated superabsorbent yarn having a layer which functions as a topsheet. In still a further alternative embodiment, the absorbent article consists essentially of the superabsorbent yarn and any yarn fastening components. Those of ordinary skill in the art will better appreciate the features and aspects of such embodiments, and others, upon review of the specification.

BRIEF DESCRIPTION OF THE DRAWINGS

A full and enabling disclosure of the present invention is set forth more particularly in the remainder of the specification, including reference to the accompanying figures, in which:

FIG. 12 is a top plan view of an alternative embodiment of the invention in the form of a hygienic pad without wings, or liner.

FIG. 13A is an alternative cross-sectional view of FIG. 12 taken along line Y"-Y".

FIG. 13B is an alternative embodiment of the cross-sectional view of FIG. 13A, without a backsheet 146.

FIG. 14 is a top plan view of an alternative embodiment of the invention in the form of a feminine hygienic pad with signal windows.

FIG. 24 is an alternative embodiment of yarn placement in absorbent articles of the invention.

FIG. 25 is an enlarged view of a portion of FIG. 24.

FIG. 26 is a top plan view of an absorbent wipe in accordance with the invention.

DETAILED DESCRIPTION OF PREFERRED EMBODIMENTS

Figure 1:
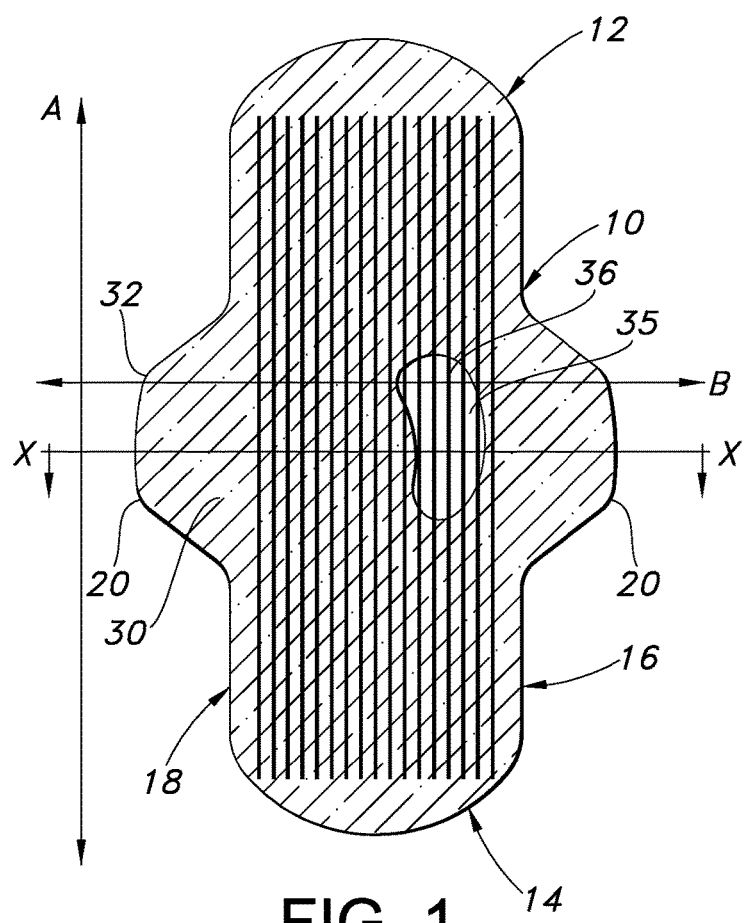
FIG. 1 is a top plan view of an embodiment of the present invention in the form of a feminine hygienic pad.

Reference will now be made in detail to present embodiments of the invention, one or more examples of which are illustrated in the accompanying drawings. Each example is provided by way of explanation of the invention and not a limitation of the invention.

In fact, it will be apparent that modifications and variations can be made in the present invention without departing from the scope or spirit thereof. For instance, features illustrated or described as part of one embodiment may be used on another embodiment to yield a still further embodiment. Thus, it is intended that the present invention covers these and other such modifications and variations as come within the scope of the appended claims and their equivalents.

For the purposes of this disclosure, the terms "superabsorbent polymer," "superabsorbent" or "SAP" shall be used interchangeably and shall mean polymers that can absorb and retain extremely large amounts of a liquid relative to their own mass. Water absorbing polymers, which are classified as hydrogels when cross-linked, absorb aqueous solutions through hydrogen bonding with water molecules. A SAP's ability to absorb water is a factor of the ionic concentration of the aqueous solution. SAPs are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAPs may be present in absorbent articles in particle or fibrous form.

For the purposes of this disclosure, the term "sliver-formed yarn" shall mean yarn formed from a continuous strand of loosely assembled filaments or fibers without a twist. The yarn itself has a twist, but the sliver does not. Sliver filaments or fibers are delivered by a card, comber or drawing frame. The production of the sliver for the yarn, is the first step that brings staple fiber into a form that can be drawn and eventually twisted into a spun yarn. Such yarn can include at least sliver filaments containing SAP materials and sliver filaments not containing SAP materials, but including fluid permeable materials or components that can assist in the distribution of fluid along the yarn length.

For the purposes of this disclosure, the term "coated superabsorbent yarn" shall mean a fibrous or filamentous yarn that has been coated (via any of a number of processes) along at least a portion of its externally facing surface with a superabsorbent polymer. The coating may be homogenous, heterogeneous or partial. The non-coated portion of the yarn includes at least fluid permeable materials or components that can assist in the distribution of fluid along the yarn length.

For the purposes of this disclosure, the term "yarn" shall mean a continuous length of interlocked fibers or filaments (as opposed to individual filaments which are extruded in a continuous manner) suitable for use in the production of textiles or nonwoven structures (woven or nonwoven), such as by sewing, crocheting, knitting, stitching, weaving, embroidery, rope making, adhesive, thermal or ultrasonic bonding. The term "yarn" shall include spun-based yarn which can be made by twisting or otherwise bonding staple fibers together to make a cohesive thread. The term yarn, may for the purposes of this definition include ribbon-like materials, and strand materials having various cross-sectional shapes, such as round, oval, elliptical, square, rectangular and irregularly defined shapes. The term yarn, does not describe a planar sheet-like material.

Desirably in one embodiment, such yarns include staple fibers of between about 0.05 and 6 inches. In a further embodiment, such yarns include between about 5 and 50 twists per inch. Desirably in another embodiment, such yarn has a decitex of between about 200 and 12000. Matrices made from such yarn may be created by nonwoven processes (thermo, adhesive or ultrasonic bonding), weaving, knitting, tow, carding, sliver, or scrim manufacturing methods.

For the purposes of this disclosure, the term "superabsorbent yarn" shall mean a yarn, as opposed to a fiber or filament, that includes superabsorbent associated directly with its structure, such that the superabsorbent is attached to or contained within the yarn structure and the yarn including at least other materials or components that are fluid permeable and which assist in holding, wicking or distributing fluid along the yarn length. The term "superabsorbent yarn" includes superabsorbent coated yarn, that is a yarn that has been coated either by a homogeneous, heterogeneous or partial coating of superabsorbent polymer, such as the yarns described in U.S. Pat. No. 5,264,251 to Geursen, U.S. Pat. No. 6,500,541 to Schoeck, Jr., and international references EP0784116 to Geursen, and WO 97/43480 to Phillips which are hereby incorporated by reference in their entirety; sliver-formed yarn with superabsorbent particles, fibers or filaments contained therein such as those described in EP 1198628 (U.S. Pat. No. 6,576,338) to Meijer which is hereby incorporated by reference in its entirety; encapsulated yarns with superabsorbent materials contained therein (either in a core entirely made from SAP, or in core made of a combination of SAP and non-SAP materials) surrounded by fluid permeable material, (such as Dref spun yarns) described in US20080096017 to Patrick and US20090176422 to Patrick, and which are hereby incorporated by reference in their entirety; multi-layered encapsulated yarns having at least three layers, that is yarn having distinct components in multiple homogenous layers in the Z direction of the yarn cross-section, with each layer provided with different absorbency or liquid transfer/distribution functionality; and yarns produced from spunbond filaments with SAP internal components such as those filaments described in US20050130540 to Crane, and which is incorporated by reference herein in its entirety. The superabsorbent yarns contemplated in the invention include either superabsorbent particles or filaments as the superabsorbent components, and non-SAP fibers or filaments that are comprised of structures/compositions that are fluid permeable, and can either retain fluid within their structures (as well as within the SAP particle and filament materials), or assist in transferring or distributing fluid along the length of the yarn to other fibers or filaments, or SAP materials. Such non-SAP components of the yarn can also assist in preventing the release of SAP materials to areas outside of the absorbent articles containing the superabsorbent yarn. The yarn may include other components to provide additional functionality to the absorbent article, such as for example, pigments for stain masking, fragrances for odor control, and color change chemistries for signal functionality.

Superabsorbent materials that can be used in the superabsorbent yarn include but are not limited to modified hydrophilic polyacrylate, starch grafted copolymers or cross-linked methylcellulose. Blending SAP materials either in a core for an encapsulated superabsorbent yarn or as part of a sliver-formed yarn, can be accomplished by blending SAP with conventional fibers such as for example, cotton, rayon, flax, jute, knaf, ramie, polyester, polyolefin (for example bicomponent materials), polyamide, acrylic, polyethylene, polylactic acid (PLA) and polytrimethylene terephthalate (PTT) fibers and blends thereof. The encapsulation component of an encapsulated superabsorbent yarn can be manufactured for example from fibers/filaments of cotton, rayon, flax, jute, knaf, ramie, polyester, polyolefin, polyamide, acrylic, polyethylene, PLA, PTT and blends thereof.

For the purposes of this disclosure, the term "free strand superabsorbent yarn", shall mean a strand of superabsorbent yarn that is either bonded to another non-yarn surface, or loosely positioned on another non-yarn surface, without the yarn being bonded to another superabsorbent yarn or contacted by another superabsorbent yarn strand that is oriented in either the same or different direction.

For the purposes of this disclosure, the terms "matrix" or "matrices" shall refer to more than one superabsorbent yarn strand that has been attached or otherwise bonded to another such strand or intersects/ contacts another such strand in one or more directions, such as in a grid-like structure, in which a series of transversely directed strands are laid over a series of longitudinally directed strands. Bonding may be accomplished using any number of bonding techniques, such as for example, adhesive, thermal, ultrasonic, needling or stitch bonding.

Side-by-side placed free strand superabsorbent yarn may include similar yarns (of dimension, denier or composition) or different yarns. Likewise, matrices made from the superabsorbent yarns may be made from various denier fibers/filaments, various denier yarns, different dimension yarns, or yarns of different compositions. Further, the placement of yarn in matrices may be controlled to incorporate yarn in specific localized bundles, fluid reservoirs on the yarn ends, non-uniform yarn crossings to control lateral spreading of fluid, greater yarn concentration in the article longitudinal direction rather than the transverse direction to utilize the farthest areas of absorbent portions, and non-straight lay down of yarn strands (such as sinusoidal (wave) or other zig-zag configurations) to enhance SAP surface area of the yarn in any given area. The fibers or filaments of such yarns may be staple, continuous, mono or multi filamentous-based. The yarns may be designed to achieve differing attributes or functionality, such as differing dryness, intake, distribution and retention attributes, or to incorporate other functionality, such as for example signal, stain masking, softness and odor control. The free strand superabsorbent yarn or yarn matrices may additionally be placed in only select areas of a plane or absorbent portion, or within multiple planes within a product.

The present invention relates generally to an absorbent article including an absorbent portion for absorbing and retaining body fluids or exudates. In many instances the absorbent article will include multiple layers with a superabsorbent yarn either on, or between the layers and positioned substantially along one or more directions of the absorbent portion of the article, or along substantially one or more directions of the absorbent article itself. The superabsorbent yarn can be present in free strands or either woven or fashioned into a matrix before it is placed in an absorbent article, or alternatively it can be adhesively bonded or otherwise bonded as a matrix or free superabsorbent yarn strands in the article. The resulting open area of the absorbent portion of the article can vary by changing the superabsorbent yarn density per unit area of the absorbent portion. Additionally, the types of superabsorbent yarns themselves can be varied in an absorbent article, depending on product area needs. In some embodiments, the absorbent portion of the article will be comprised of solely the superabsorbent yarn itself, for example, in strands or in adhered strands that have been cut and fashioned/ adhered to themselves, in the shape of a traditional absorbent article. By using a yarn construction by itself as the absorbent portion of an article, without supplemental fluid retention components or layers, the level of breathability and flexibility of the absorbent article can be increased. Further, it is possible to direct exudates to specific regions of an article for efficient usage of the entire absorbent portion of the article, by use of the superabsorbent yarn.

Figure 2:
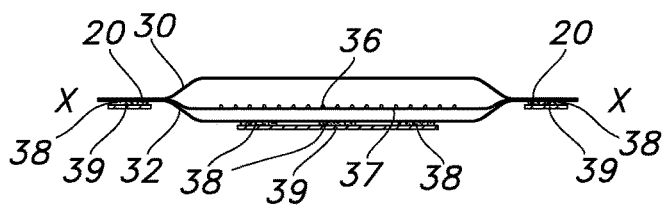
FIG. 2 is a cross-sectional side view of an alternative embodiment of the present invention of FIG. 1 taken along line X-X of FIG. 1.

The accompanying FIG. 1 depicts a top plan view of an absorbent article 10 of the present invention as a hygienic feminine pad having a conventional elongated shape with generally rounded ends; however, the absorbent article 10 may also be a panty liner, tampon, shield, diaper, training pant, adult incontinent garment, wipe, bandage, or any other disposable absorbent article known in the art, many of which are illustrated in later appearing figures. Moreover, the illustrated pad absorbent article 10 may have other shapes, such as hourglass, dogbone, elliptical, triangular or rectangular, and varying sizes and thickness, depending on the particular application desired. The absorbent article 10 generally includes two end edges 12 and 14, two longitudinal directed side edges 16 and 18, and two optional wing or flap extensions 20 extending from the longitudinal directed side edges 16 and 18. The wings may be integral with the pad structure, that is, extensions of layers in the pad structure, or add-on features. The article 10 includes a topsheet or cover layer 30 which faces the skin of a user during use and which first receives body exudates from a user, and a backsheet or baffle layer 32, which is normally positioned away from the skin of a user and often faces and contacts a user's undergarments or outergarments. An absorbent portion/layer 35 is positioned between the topsheet 30 and the backsheet 32 and includes at least superabsorbent yarn strands 36 as viewed through the partial cut-away hole in the figure. In the figure, the free strands 36 are illustrated running in parallel lines along the longitudinal direction A of the article. It should be recognized that the strands could in an alternative embodiment, also run in the transverse direction B of the article or a combination of the longitudinal and transverse directions. Further, the yarn strands 36 may run in a non-straight fashion, such as in a wave, zigzag or other configuration in either a uniform, nonuniform or random direction (intersecting or nonintersecting), or a combination of any of the above patterns. Such wavy or zig-zag patterns can provide more absorbent surface area than straight laid yarn strands. The superabsorbent yarn strands 36 can be adhesively bonded directly to the inside surface of the backsheet 32 facing the topsheet 30, to the inside surface of the topsheet 30, facing the backsheet 32, or as shown in FIG. 2, which shows a cross-sectional view of an alternative embodiment of the article of FIG. 1 at line X-X, the superabsorbent yarn strands 36 can be adhesively or otherwise bonded to a carrier sheet 37, which is itself bonded to an inside surface of the topsheet 30 or backsheet 32. In FIG. 1, no carrier sheet is illustrated, and the strands are sandwiched between the topsheet 30 and the backsheet 32. The carrier sheet 37 may be positioned solely on one side of the superabsorbent yarn strands (as illustrated in FIG. 2), or may partially or entirely envelop the yarn strands, such that the yarn strands are sandwiched between carrier sheet layers. Additionally, more than one carrier sheet may be positioned along one side of the yarn strands. Such carrier sheet(s) may serve as a protective layer to isolate the superabsorbent yarn strands or the superabsorbent components themselves, especially for preventing SAP from migrating to other areas of the product, but to still allow fluid to make contact with the yarn strands. Additional bonding techniques may include needling or thermal bonding as well, for attachment of the yarn strands to the carrier sheets or adjacent layers. The carrier sheet may be constructed of traditional materials such as a tissue or other nonwoven material, as are known in the art. In an alternative embodiment, additional intermediate layers may be positioned between the yarn and carrier sheets and either the topsheet or backsheet. Further, such superabsorbent yarn can wrap around such layers or through such layers to direct fluid in various directions within an article.

As can be further seen in FIG. 2, garment adhesive strips 38 or other fasteners can be positioned along the longitudinal direction of the product central region and/or wings 20 for adherence of the article to a user's undergarments in use. Such adhesive strips 38 can be covered with adhesive release sheets 39 for covering the adhesive strips before use, and then removed at the time of use. The adhesive strips along the backsheet center of the product would function to adhere the product to the inside crotch region of a user's undergarments or outergarments, while the adhesive strips on the wing backsheet areas would provide temporary attachment to the opposite side of the undergarment crotch region once the wings had been folded about the side edges of the undergarments during use.

The topsheet 30 provides the absorbent article 10 with a liquid/fluid permeable surface that contacts the user's skin. The topsheet 30 should provide a comfortable, conforming interface with the user's skin by being flexible, compliant, and non-irritating to the skin. The topsheet 30 desirably also transfers liquid/fluids quickly to underlying layers and remains dry and clean during use, effectively reducing or eliminating the feeling of rewet during use. In addition to being liquid permeable, the topsheet 30 may also include apertures (not illustrated) for freely passing exudates with minimal absorption. The topsheet 30 may be coated with a surfactant to further enhance permeability to the absorbent portion 35 and reduce retention of fluids by the topsheet 30, or it may be coated or otherwise imbued with other skin-health treatments. The topsheet 30 may also include embossments (not illustrated) such as embossed channels, and arcuate embossments, to create an aesthetically pleasing surface, a particular product bend profile or to further help disperse exudates passing through the topsheet 30, or alternatively to slow their spread to the product side edges. Furthermore, if so desired, these embossments may extend down into one or more other layers of the product to enhance the fluid handling properties of the product and may further serve to attach the topsheet 30 to subjacent layers in the article.

The topsheet 30 may be constructed of any woven or non-woven material which passes body fluids, yet remains comfortable to the user. Suitable nonwoven materials include, but are not limited to, hydroentangled spunlace materials, bonded carded webs (BCW) made from staple fibers, and spunbond webs. Apertured films are also suitable topsheet materials. Examples of suitable topsheet materials include rayon, bonded carded webs of polyester, polypropylene, polyethylene, nylon, or other heat-bondable fibers, polyolefins, copolymers of polypropylene and polyethylene, linear low-density polyethylene, and aliphatic esters such as polylactic acid.

Other suitable topsheet materials include through-air bonded carded webs (TABCW) made from staple length fibers such as 25 gram per square meter (gsm) web made with 1.5 denier (d), polyethylene sheath, polypropylene core bicomponent, 35-40 millimeter (mm) staple length fibers available from FiberVisions Corporation with offices in Duluth, Ga., USA which are available under the trade designation ESC215. Topsheet materials may also comprise laminates of the above materials, and are desirably bonded to the inside surface of the backsheet 32. The topsheet 30 may also be made from two or more different nonwoven or film materials. For example, the topsheet may be a multi-component material with a central section (not shown) running along and straddling the longitudinal centerline of the product with lateral side sections (not shown) flanking and joined to either side of the central longitudinal section. The central section may be made for example, from the aforementioned TABCW materials or it may be made from a perforated film. The lateral side sections may be made from a different fibrous nonwoven material which is joined to the central section. Such a dual material configuration is described for example in U.S. Pat. No. 5,961,505 to Coe, U.S. Pat. No. 5,415,640 to Kirby and U.S. Pat. No. 6,117,523 to Sugahara, which are hereby incorporated by reference in their entirety. Such a dual material or bicomponent topsheet could offer the feeling of dryness in the center longitudinal region, and a soft feeling along the side longitudinal regions. It is also contemplated that such dual material topsheets may include elastic components along their side edges to lift up portions of the side materials during use, thereby forming physical barriers or a cupping feature of the product so as to fit closely to the body.

Topsheet materials with larger open areas are desired in one embodiment in order to provide visibility to the superabsorbent yarns beneath the layer. As shown in the figures, it is desired that at least part of the topsheet be translucent so as to allow a user of the product to observe the functionality of the superabsorbent strands (via a change in color from dry to soiled yarn). Such may be further achieved by wide apertures in the topsheet, which also allow exudates to flow quickly to the superabsorbent layers contained beneath the topsheet layer.

In the illustrated embodiments in FIGS. 1 and 2, the free superabsorbent yarn strands 36 make up solely the absorbent portion of the article. That is, there are no other liquid retention layers in the article. In such an embodiment, the superabsorbent yarn strands provide flexibility to the article, that an absorbent sheet material would not. Further, such a configuration provides enhanced thinness and breathability to the article. Alternatively, the superabsorbent yarn strands 36 may be a component of the absorbent portion, which could also include cellulosic or synthetic fibrous wadding layer(s), a multilayered structure, such as one that includes a surge or transfer layer, a distribution layer or a combination thereof. These other layers while not illustrated, are well known in the art. These supplemental layers can be employed in the absorbent article either in the same plane as the superabsorbent yarns, or alternatively in a plane above or below the superabsorbent yarns. A surge or transfer layer provides an optional layer between the topsheet layer and the absorbent core (portion). When present, a transfer layer wicks fluid passing through the topsheet layer and disperses the fluid to subjacent layers including the absorbent core. The transfer layer may comprise any of the fibers, polymers and fibrous and film structures mentioned above with respect to the topsheet material as well as any surge materials as are readily available and well known to those of ordinary skill in the art. No matter which surge layer material is being used, the surge or transfer layer can run the full length of the product or it may be shorter and strategically located in a specific area of the product. In addition, it can be a full width layer extending to the longitudinal sides of the product or it may have a shorter width in which case it will generally be centered on the longitudinal centerline of the product.

Further, as will be further explained, the superabsorbent yarns may also be part of one or more matrices, as opposed to being present in a free strand configuration. For the purposes of this invention, in some embodiments it is desirable to minimize contact of individual yarn strands (with one another) within an absorbent article, so as to prevent interference of SAP that may swell in one strand with fluid movement on another strand. In this regard, in one embodiment, it is desirable that the percent contact/overlap of one strand with another separate strand be between 0 and 100 percent, in at least one strand dimension. At 0% (no contact of individual strands), the discrete yarn strands allow fluid to be transferred within each individual strand such that the performance of each strand does not impact that of the others. The space between strands helps to drain fluid to the strands. At some overlap of strands (up to 100%), the strands can overlay each other in separate layers. In such an embodiment, the yarn type on each layer can serve different functions such that they do not affect the performance of each other. For example, a top layer can be for intake and distribution functionality whereas a bottom layer can be for containment/storage functionality.

The back sheet 32 may be peripherally joined to the top sheet 30 either directly or indirectly through intermediate layers, usually about the periphery of the article. It provides the absorbent article 10 with a liquid impermeable and optionally vapor permeable surface that prevents exudates from completely penetrating the absorbent article 10 and soiling the user's undergarment or outergarments. Ideally, the backsheet 32 is soft, flexible, quiet, breathable, and may in one embodiment include some absorbent capacity on the side facing the absorbent portion 35.

The backsheet 32 may be any suitable material known in the art, such as embossed and non-embossed thermoplastic films, nonwoven webs, laminated tissue, and combinations of the foregoing. In one embodiment, the backsheet 32 includes a non-woven material laminated to a microporous film with the nonwoven material forming a soft and comfortable exterior surface to the absorbent article 10. Desirably, such backsheet film materials can haves a thickness of between about 0.03 to 0.07 mm and demonstrate a water vapor transmission rate (WVTR) of between about 500 to 2500 g/m 2/24 hr. The backsheet can be transparent, translucent or opaque depending on the product needs. In order to enhance the signaling effect of the superabsorbent yarns, and perception of thinness and breathability of the product, transparent and translucent backsheet materials may be preferred. For aesthetic appeal, printed features may also be included on the backsheet.

Construction adhesives to be used in the products of the invention can be those common to the art of personal care products. However, in product embodiments with apertured topsheets, non-tacky adhesives might be more desirable.

The absorbent portion 35 provides the operative material for collecting and retaining body fluids or exudates while remaining light and dry feeling during use. The absorbent portion 35 should in one embodiment be soft, not stiff, and should retain its shape, even when wet. The absorbent portion 35 resides between the topsheet 30 and the backsheet 32 and may be attached to either or both layers or to intermediate layers such as the optional surge layer or carrier sheet to hold the absorbent portion 35 in place and protect the absorbent portion 35 from abrasion.

The absorbent portion of the absorbent article may be any structure or combination of components with the superabsorbent yarns 36 which are generally compressible, conformable, non-irritating to the user's skin, and capable of absorbing and retaining bodily fluids. For example, the absorbent portion with superabsorbent yarns may include an absorbent web of cellulose fibers, such as wood pulp fibers, other natural fibers, synthetic fibers, woven or non-woven sheets, scrim netting or other stabilizing structures, additional superabsorbent materials separate from the superabsorbent yarns, binder materials, surfactants, selected hydrophobic and hydrophilic materials, pigments, lotions, and odor control agents, as well as combinations thereof. The absorbent portion may be formed using various methods and techniques known in the art, such as dry-forming, air forming, wet-forming, and foam-forming, as well as combinations thereof.

As previously stated, superabsorbent materials are well known in the art and may be selected from natural, synthetic, and modified natural polymers and materials. The absorbent portion 35 with superabsorbent yarns 36 generally includes superabsorbent material, with the superabsorbent material ranging from about 1-90 percent by weight of the absorbent portion 35, depending on the application and desired absorbency. For example, the total absorbency may be about 200-900 grams of 0.9% by weight saline for infant care products; whereas, the total absorbency for adult care products may be about 400-2000 grams of 0.9% by weight saline. For feminine care products, the total absorbency may be within the range of about 7-50 grams of menstrual fluid. In one embodiment, the superabsorbent is present in an amount of between about 10 and 50 percent by weight of the yarn. Optionally, the absorbent portion 35 may include what is termed a core wrap (not shown) made from tissue or a nonwoven sheet such as a spunbond or a meltblown nonwoven or a laminate of spunbond and meltblown layers, the purpose of which is to aid in retaining the superabsorbent yarn and yarn components neatly within the absorbent portion area and increasing both the wet and dry strength and integrity of the absorbent portion 35. The core wrap would envelop all or a portion of the absorbent portion 35. Such a core wrap may be useful to enclose superabsorbent yarn that contains superabsorbent fibers or particles on the yarn outer surface.

Referring again to FIG. 1, the absorbent article 10 may optionally include what are termed a pair of wings or flaps 20 extending laterally from the central portion (or end portions for thong and overnight products, but not illustrated) of the product. Such wings or flaps 20 are well known in the art and may be integrally formed from other components of the article such as the topsheet 30 and backsheet 32, or from separate materials and then attached to the longitudinal sides 16, 18 of the article 10.

The various layers of the absorbent article may be joined or not joined to one another depending on the design criteria of the specific product. In this regard, any conventional joining techniques may be used including, but not limited to, adhesives, bonding and embossing techniques using heat and/or pressure, ultrasonic bonding, needling, stitching, hyrdoentangling, etc. In most instances, it is desirable to seal one or more layers together about the periphery of the product so as to reduce leakage of absorbed body fluids.

The superabsorbent yarns 36 are shown in FIG. 1 through a cutaway portion of the topsheet 30, but also through the topsheet 30 surface itself. In one embodiment, the topsheet is at least partially translucent to allow a user to see the soiling of the absorbent portion along the length of the superabsorbent yarns 36 during use. For the purposes of this application, the term "translucent" shall mean the ability of a user with legally defined sight, to view color changes of the superabsorbent yarn through the topsheet, when viewing the user facing surface of the article unobstructed from a distance of between one and sixty inches. The visualization of the spread of fluid along the length of the yarn is accomplished by the natural color change of the absorbent materials in the superabsorbent yarn as body exudates are absorbed by the yarn. In this fashion, a user of the product can clearly see the level of product usage in anticipation of avoiding a potential leak, without additional chemical signals. Alternatively, the topsheet may be opaque or contain masking elements (such as pigments in the fibers or film) so as to avoid providing such information to users that would prefer not to see it.

Figure 3A:
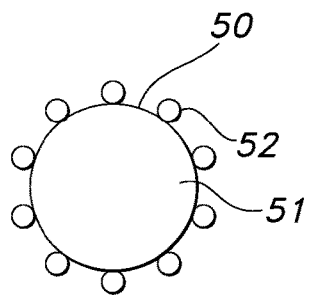
FIG. 3A is a cross-sectional view of a superabsorbent yarn that may be used in the present invention.

As noted previously, various types of superabsorbent yarns may be employed in absorbent portions of absorbent articles of the invention. For example, as shown in cross-sectional view of FIG. 3A, a yarn 50 of fibers/filaments along its longitudinal body 51 may be coated along its surface with superabsorbent particles 52 or fibers. The yarn is shown in stylized format, but it should be understood that the yarn body itself 51, may be twisted, such as in a traditional "S" or "Z" configuration or crimped to further impart bulk or texture, or additional interstitial space for fluid flow. In such a configuration, the central yarn body can be made of fibers such as from fluid permeable materials and the superabsorbent fibers or particles can be adhered to the yarn by blending, chemical binder, charge attraction or other traditional bonding method. The non-SAP fibers/filaments are desirably fluid permeable such that they either hold fluid, or distribute fluid along the yarn length.

Figure 3B:
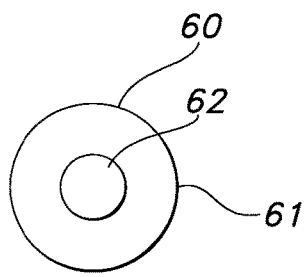
FIG. 3B is a cross-sectional view of a different superabsorbent yarn that may be used in the present invention.

Alternatively, as can be seen in FIG. 3B, the superabsorbent yarn 60 can include an outer fluid permeable layer 61 which encapsulates a central superabsorbent material containing core 62. In such an encapsulated superabsorbent yarn, or a yarn made from encapsulated superabsorbent fibers, the superabsorbent material is less likely to migrate out of the yarn to the other portions of the article or to the consumer's skin surfaces. In such an embodiment, the need for a separate carrier layer 37 is reduced, especially one that completely envelops the yarn on both sides. Further the outer fluid permeable layers of the yarn can act as a fluid intake or distribution layer before bulk fluid is locked into the superabsorbent core material of the yarn or filaments in the yarn. The nonwoven outer layers can also be tailored to achieve particular fluid handling properties, by selection of porosity, fiber type, fiber size, varying fiber twists between the outer and core layer(s) etc. For example, fibers may be varied depending on the ultimate objective of absorbing urine waste, bowel movement waste, menstrual waste or wound exudates. Fiber affinities to various fluids may vary depending on components of the fluid to be absorbed, such as affinities to proteinaceous fluids or ion/salt containing fluids. Further, the cotton count of any yarn that is selected to be part of a matrix (such as a woven pattern) will also impact the flexibility of the yarn. Therefore, if matrices of superabsorbent yarn are to be used in a product, one or more types of matrices can be used with variations in size, open area, core composition, outer layer composition and layering to provide different levels of fluid handling and body fit at different locations in an absorbent article. Such varying matrices can be placed in either the same plane/layer or differing planes/layers within the absorbent article. For example, in any given plane of an absorbent portion of an article, a central region can comprise a rapidly wicking yarn, while the edges of the plane can be comprised of yarns with better fluid retention capabilities, that is the ability to hold onto the absorbed moisture, rather than focusing on initial bulk absorbency characteristics. Depending on the desired fluid handling features of the article, it is envisioned that the absorbent matrices can also include absorbent yarns without SAP, such as yarns from polyester, rayon and nylon materials, but in combination with such SAP yarns. Further, traditional absorbent materials can be used in conjunction with the superabsorbent yarns, such as airlaid materials, through air bonded carded webs, SAP planar sheets, hydroentangled materials, and chemically bonded carded webs. As with the yarn of the previous figure, the yarn of FIG. 3B may include varying twists, either in its entirety or between layers, or additional crimping.

Figure 3C:
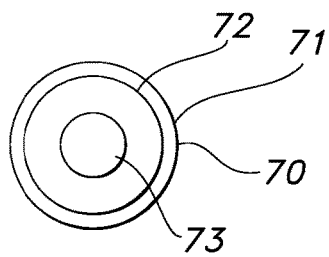
FIG. 3C is a cross-sectional view of still a different superabsorbent yarn that may be used in the present invention.

Alternatively, as can be seen in FIG. 3C, the superabsorbent yarn 70 can include multiple layers in the Z cross-sectional direction (depth direction). Such outermost layers would be fluid permeable, with each layer itself functioning as a traditional layer in an absorbent article. For example, the outermost layer 71 can be comprised of fibers that would normally make up either a topsheet or initial surge or transfer layer of an absorbent article. Such outermost layer can be made of traditional topsheet layer fibrous materials if the absorbent article containing the yarn does not include a separate topsheet layer (as described further in FIGS. 13A and 13B). The outermost layer 71 can alternatively be made of fibers that would normally make up either a surge layer or transfer layer, if the article containing the yarn would include a separate topsheet layer. In this fashion, as fluid is drawn into the yarn, it would pass through a traditional surge or transfer layer along the yarn's entire length. Beneath the surge layer 71 (or topsheet layer as the case may be), at least one interior absorbent layer can be positioned along the yarn's length 72. Such absorbent layer can be positioned continuously along the yarn's length or discontinuously along the yarn's length. Finally, within the center of the yarn, a superabsorbent containing secondary core can be positioned 73 along the yarn's entire length, or alternatively discontinuously along the yarn's length. In this fashion, a self-contained absorbent system can be configured into a single yarn strand that can be cut to a desired length and placed strategically in an absorbent article of the present invention. Such absorbent outer layers 72 can be comprised of traditionally used absorbent fibrous materials. Such multiple layered yarns can be manufactured using Dref spinning systems as those previously noted herein. It should be recognized that several absorbent and other functional layers may be employed in such yarns to achieve the desired level of absorbency and distribution along the entire yarn strand length. Such layering would of course be dependent on the type of body exudates being absorbed and the type of absorbent article desired. For example, an absorbent system designed to wick menses may employ different materials than one designed to wick urine or bowel movements. As with the previous figures, such yarn may also include a variety of twists depending on layer, as well as crimping.

Figure 3D:
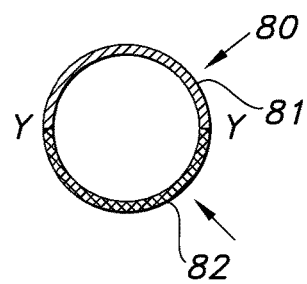
FIG. 3D is a cross-sectional view of still a different superabsorbent yarn that may be used in the present invention.
Figure 4:
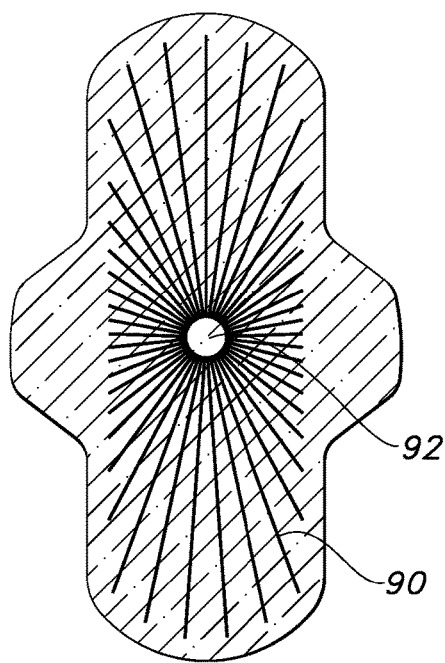
FIG. 4 is a top plan view of another embodiment of the present invention in the form of a feminine hygienic pad.
Figure 5:
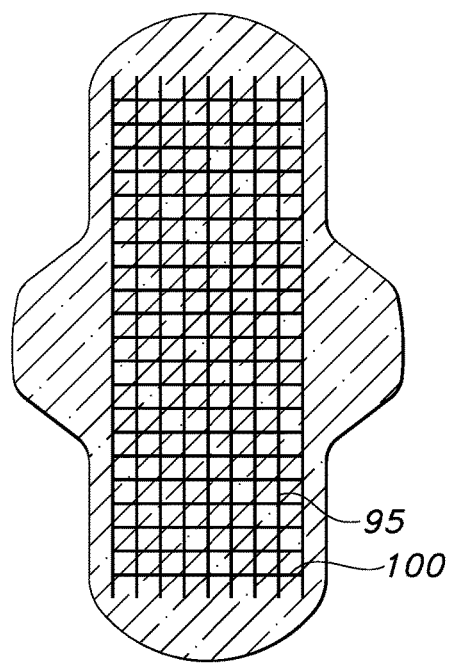
FIG. 5 is a top plan view of still another embodiment of the present invention in the form of a feminine hygienic pad.
Figure 6:
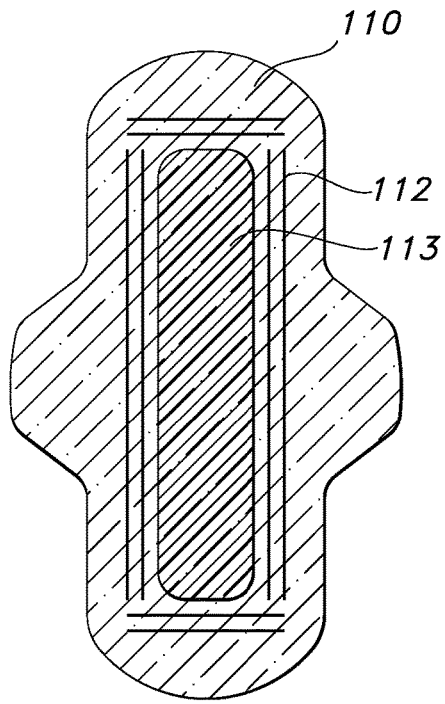
FIG. 6 is a top plan view of still another embodiment of the present invention in the form of a feminine hygienic pad.
Figure 7:
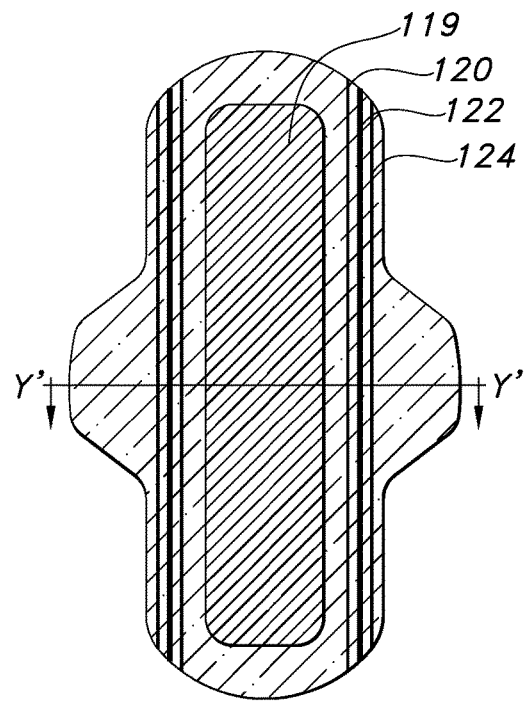
FIG. 7 is a top plan view of still another embodiment of the present invention in the form of a feminine hygienic pad.
Figure 8:
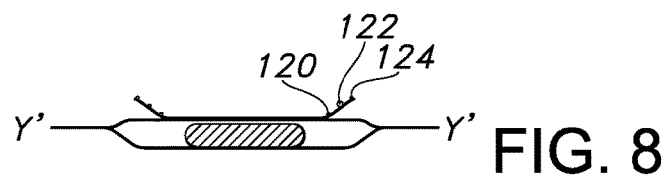
FIG. 8 is a cross-sectional view of the embodiment of FIG. 7 taken along lines Y'-Y'.

As can be seen in FIG. 3D, such superabsorbent yarn strands 80 may include surface treatments along the Y-Y axis, depending on yarn placement in an absorbent article. For example the upper surface that faces a user may include a hydrophilic finish 81, while the lower surface finish 82 facing away from a user towards a garment, may employ a hydrophobic surface treatment. Such surface treatment materials are known in the absorbent art and will not be further described. While the superabsorbent yarn strands 36 are shown in a parallel linear configuration along the absorbent article's longitudinal direction in FIG. 1, it should be appreciated that such a configuration is meant for example only. Other configurations may be more desirable, depending on product usage. For example, as seen in the top plan view shown in FIG. 4, an alternative embodiment of a feminine hygienic article (pad) includes such visible free superabsorbent yarn strands 90 positioned between a topsheet and a backsheet, but in a star-burst pattern such that fluid is wicked to all perimeter areas of the article from a centrally located fluid deposition area 92. Some of the strands 90 would be cut of a longer length to accommodate the longer distances to the outer periphery of the product. As can be seen in the top plan view of a feminine hygienic article of FIG. 5 showing a further alternative embodiment, in an alternative, such visible superabsorbent yarns can be configured into a grid-like matrix along the product between the topsheet and the backsheet, so as to wick exudates across both the longitudinal 95 and transverse 100 yarn directions of the product. As can be seen in a further alternative embodiment of a feminine hygienic article of FIG. 6, visible superabsorbent yarns can be positioned along the product periphery 110 between the topsheet and backsheet such that they serve as an outer barrier or boundary to prevent leakage of body exudates prior to the fluid reaching the product edges. Such a configuration could also employ the superabsorbent yarn 112 surrounding a traditional absorbent wadding layer 113, with both of the traditional absorbent layer and the superabsorbent yarns being positioned in the same plane between the topsheet layer and the backsheet layer(s). As noted previously, in some embodiments, the absorbent article may employ elastic features to elevate portions of the article. As can be seen in FIGS. 7 and 8 (FIG. 8 showing a cross-sectional view of FIG. 7 taken along line Y'-Y'), the feminine hygienic article employs a traditional wadding absorbent core 119. Such wadding can be in the form of cellulosic materials, airlaid materials, TABCWs, SAP sheets or a combination thereof. The topsheet includes both visible superabsorbent yarn strands 120 and 122 to serve as fluid barriers, and also elastic strands 124, to serve as elevating means to raise the barriers along the article side edges during use. Traditional pre-tensioned elastic strands, or liquid shrinkable elastic strands may be employed for this purpose, as are known in the personal care article art. Such strands would be adhered to either the underside or topside of the raised topsheet surface using traditional bonding methods, or alternatively, may be bonded between multiple layer topsheets in these areas.

Figure 9:
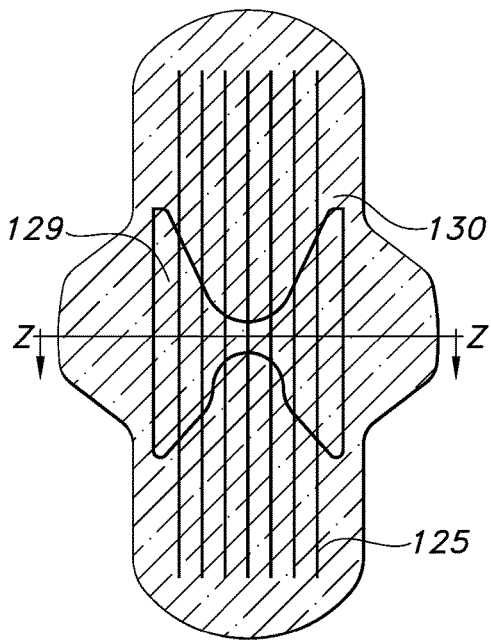
FIG. 9 is a top plan view of still another embodiment of the present invention in the form of a feminine hygienic pad.
Figure 10:
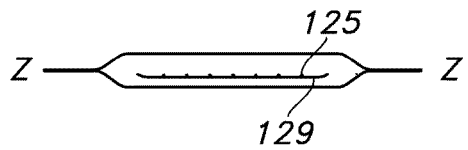
FIG. 10 is a cross-sectional view of the embodiment of FIG. 9 taken along lines Z-Z.

Referring to FIGS. 9 and 10 (10 which is a cross-sectional view of FIG. 9 taken along line Z-Z), in an alternative embodiment, a feminine hygiene article shown in top plan view contains a stabilizing member 129 for controlling the contour and bunching of the product during use, thereby providing greater stability of the product. The stabilizing member or shaping layer, as it is sometimes called, is desirably positioned either between the superabsorbent yarns 125 of the absorbent portion and the backsheet layer (with the superabsorbent yarns positioned beneath the topsheet) as illustrated, or alternatively, with the superabsorbent yarns beneath the stabilizing layer, which is closer to the topsheet (not illustrated). In the case of FIG. 9, the shaping layer is in the shape of a butterfly. A common problem with absorbent articles such as sanitary napkins is their tendency to bunch and ride up into the contours of the body including the buttocks and the vaginal area during use. Bunching reduces the effective surface area of fluid capture, increasing the likelihood of fluid leakage and staining of undergarments/outergarments. As the net-like matrices of the absorbent yarns of the present invention are highly flexible, the pad may become more susceptible to body pressure and movement, resulting in this type of bunching. In order to overcome this possibility, the addition of a stabilizing member provides extra support. The shaping layer may comprise one or more layers of materials that are positioned towards the longitudinal and transverse center lines. Such shaping layer can be rigid and fluid impermeable, but can also be fluid permeable. Such stabilizing layer can be manufactured from a variety of materials, such as for example, airlaid materials, meltblown materials, SAP sheets, fluff mats, foams, films, bulky bonded carded web materials or other material or combination of materials, which provide sufficient integrity to relieve bunching. While placement of such a layer can be anywhere in the product, it should be positioned so as not to negatively impact fluid handling attributes. Such a shaping layer can be of any size or shape although it is preferably shaped to preserve the openness of the absorbent portion. It is in one embodiment, die cut. One desirable shaping layer is an airlaid cut-out material, of between about 60 gsm to 200 gsm, that is narrowest in its center, so as to retain an openness to the absorbent portion as shown in the figure. Such a shaping layer can be either absorbent or non-absorbent.

Figure 11A:
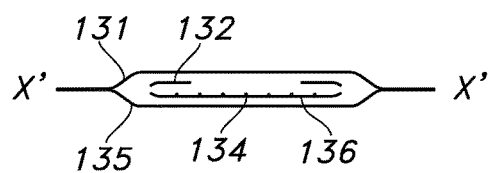
FIG. 11A is a cross-sectional view of the embodiment of FIG. 11 taken along lines X'-X'.
Figure 11:
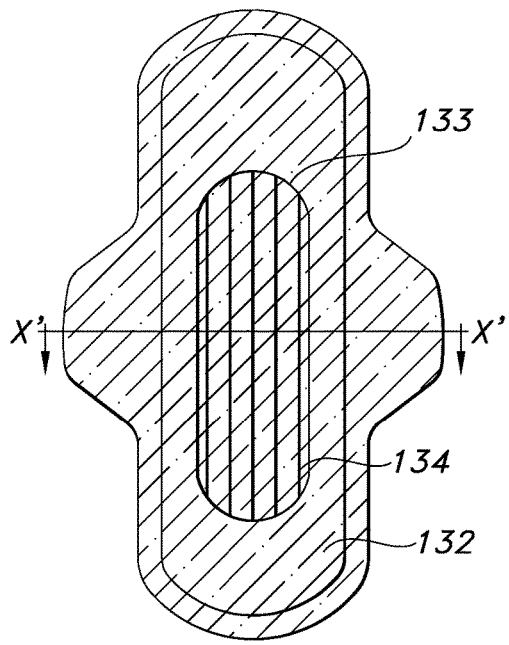
FIG. 11 is a top plan view of still another embodiment of the present invention in the form of a feminine hygienic pad.

In a further alternative embodiment of a feminine hygiene article, as shown in FIGS. 11 and 11A, an open area at the product center is created by a hole-like structure 133 defined by either an upper absorbent layer or fluid transfer/surge layer 132, which is situated beneath a topsheet 131 and above superabsorbent yarn strands 134. As can be seen in FIG. 11A, which is a cross-sectional view of FIG. 11 taken along line X'-X', such yarn is also situated upon a carrier layer 136 that is positioned between the topsheet 131, and the backsheet 135. In such an embodiment, the hole 133 contained within an upper surge or transfer layer helps to further direct exudates down to the absorbent portion, made from free superabsorbent yarn strands 134. It also helps to focus the user's attention on the strands as the upper absorbent layer or fluid transfer/surge layer 132 is opaque in one embodiment, preventing viewing of the yarn in areas outside of the hole. It should be recognized that the upper absorbent layer or fluid transfer/surge layer 132 can be formed of absorbent or surge materials known in the art.

Figure 11B:
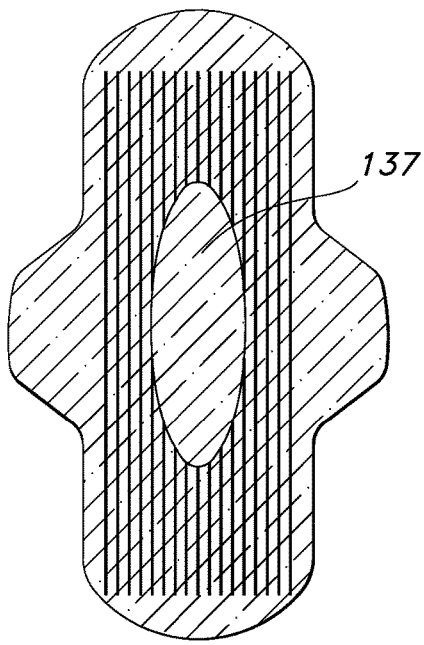
FIG. 11B is a top plan view of an alternative embodiment of the pad of FIG. 1.

In still a further alternative embodiment, as shown in FIG. 11B, a feminine hygiene article is illustrated in top plan view having a centrally placed supplemental absorbent layer 137 in an oval configuration, positioned beneath the topsheet and above parallel free superabsorbent yarn strands. In this embodiment, a hump is created by the supplemental absorbent layer 137 along the central longitudinal and transverse axis, so as to allow for closer contact of the product in the vaginal vestibule of a female consumer during use. It should be recognized that the hump or raised portion can be of any shape and of materials known in the art for absorbent layers.

Figure 11C:
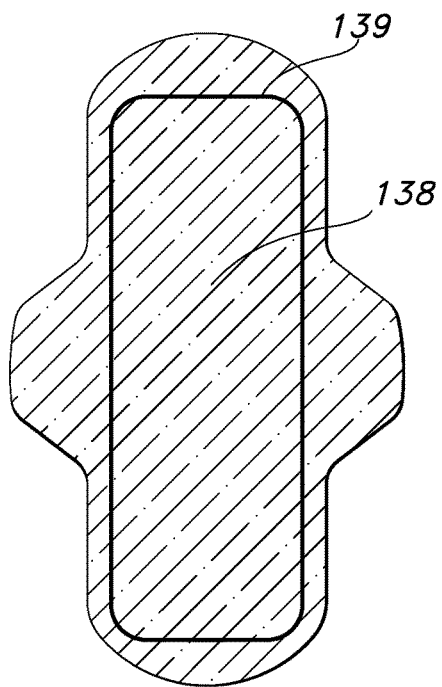
FIG. 11C is a top plan view of an alternative embodiment of the pad of FIG. 1.

In still a further alternative embodiment of a feminine hygiene article, as illustrated in FIG. 11C, a traditional absorbent layer 138 is positioned between a topsheet and a backsheet. However, a strand or multiple strands of superabsorbent yarn 139 are positioned within the same plane as the traditional absorbent layer, but surrounding the perimeter of the traditional absorbent layer 138. In this fashion, an outer wall of absorbent protection is provided in conjunction with a traditional absorbent layer 138.

Figure 11E:
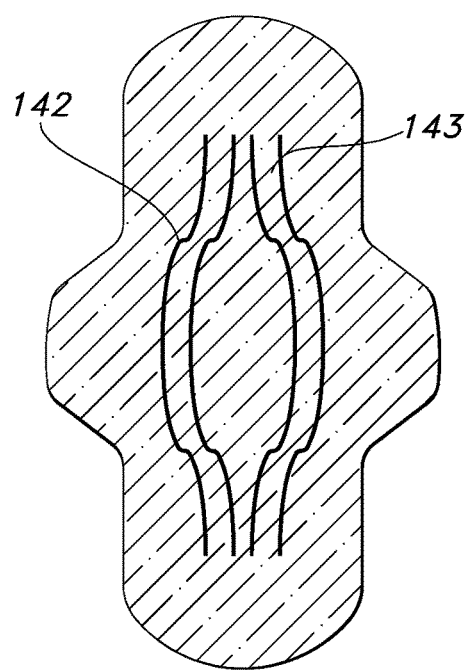
FIG. 11E is a top plan view of an alternative embodiment of the pad of FIG. 1.
Figure 11D:
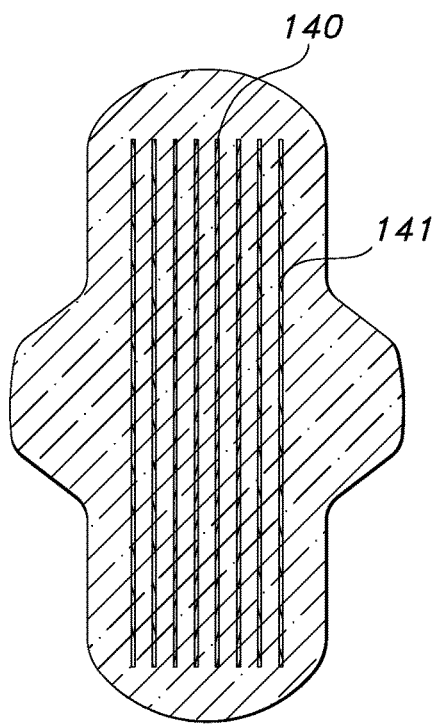
FIG. 11D is a top plan view of an alternative embodiment of the pad of FIG. 1.

In still a further alternative embodiment of a feminine hygiene article, as illustrated in FIG. 11D, different types of superabsorbent yarns can be positioned in either the same plane or different planes within an absorbent article. For example, rapidly absorbing superabsorbent yarn can be placed along the longitudinal centerline of a product 140, while greater retention capacity superabsorbent yarn 141 can be placed closer to the longitudinal side edges of an article, for example in a layer between the topsheet and backsheet of the article.

Figure 11F:
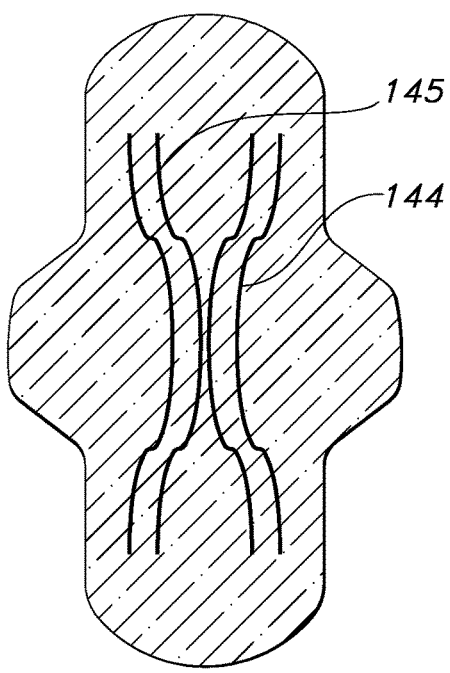
FIG. 11F is a top plan view of an alternative embodiment of the pad of FIG. 1.

In still a further alternative embodiment of a feminine hygiene article, as illustrated in FIGS. 11E and 11F, different densities of superabsorbent yarns can be positioned in different regions of a product to direct fluid to desired locations. For example, as seen in FIG. 11E, higher densities per unit area of superabsorbent yarn 142 can be positioned along a product's edges (between the topsheet and backsheet) in order to move fluid away from the sides to the ends 143 of a product, which would have the highest density of yarn in the product per unit area. Alternatively, as seen in FIG. 11F, higher densities of superabsorbent yarn can be positioned in a product center 144, between a topsheet and backsheet, to move fluid away from the center to the product ends 145.

In still a further alternative embodiment of the invention, as seen in FIG. 12, which illustrates a top plan view of a hygienic feminine care liner having a carrier or backsheet layer 146 and parallel superabsorbent yarn strands 147 adhered across the transverse direction of the liner. As can be seen in FIG. 13A, which illustrates an alternative embodiment of the liner of FIG. 12 and in particular, an enlarged view of a cross section of the alternative embodiment of FIG. 12 taken along line Y"-Y", the superabsorbent yarn strands can be stacked in layers 147 upon the liner backsheet 146. In this fashion, they can be adhesively adhered to each other and the backsheet/carrier sheet, without a separate topsheet present. If an encapsulated yarn is used as the superabsorbent yarn component, the encapsulated yarn can include an outer ring of material (as previously described) which functions as a topsheet, thereby eliminating the need to have a separate and distinct topsheet. In still a further alternative embodiment of the liner of FIG. 12, as can be seen in FIG. 13B, the carrier sheet/backsheet 146 can itself be eliminated, and the liner itself can be formed only from stacked superabsorbent yarn strands 147 bonded to each other 148 as a composite. The yarn strands can be cut to a desired length to mimic the length of a liner either before or after they are adhesively adhered, for example, to each other. The yarn strands can be adhesively bonded using an adhesive which maintains its flexibility upon drying, or alternatively, using intermittent applications of adhesive so as to not restrict yarn swelling.

In still a further alternative embodiment of the invention, a top plan view of a feminine hygiene article in the form of a pad is shown in FIG. 14. In such figure, a transfer or surge layer 150 is positioned between a translucent topsheet and an absorbent portion. Such surge layer 150 is opaque in one embodiment, shielding or masking the staining of lower layers that may become discolored from body exudates absorbed from a user wearing the article. Numerous perimeter openings or windows 151, 152, 153, and 154 are defined by the surge layer 150. A matrix of superabsorbent yarn 160 is situated beneath the surge layer and between the surge layer and the backsheet. The matrix of superabsorbent yarn 160 is only visible to the consumer through the translucent topsheet and the surge layer 150 via the openings, such that the consumer can easily observe spread of absorbed exudates in the article that were originally deposited in the central area of the pad, and recognize when the absorbed and spreading exudates are approaching or have approached the longitudinal and transverse side edges of the article, thereby taking action to change the product before potential exudate leakage, and subsequent staining of the user's undergarments. In such an embodiment, the mere color change of the superabsorbent yarn, either in actual color change or shade change as a result of insult, will provide a passive visual notification or signal of a pending leak. It should be understood that such openings can be present in any number, and in a variety of selected perimeter locations. For example, such openings may only be present adjacent the wings 152, 153 in the product transverse direction or only at the ends 151 and 154.

Figures 15, 15A, 15B:
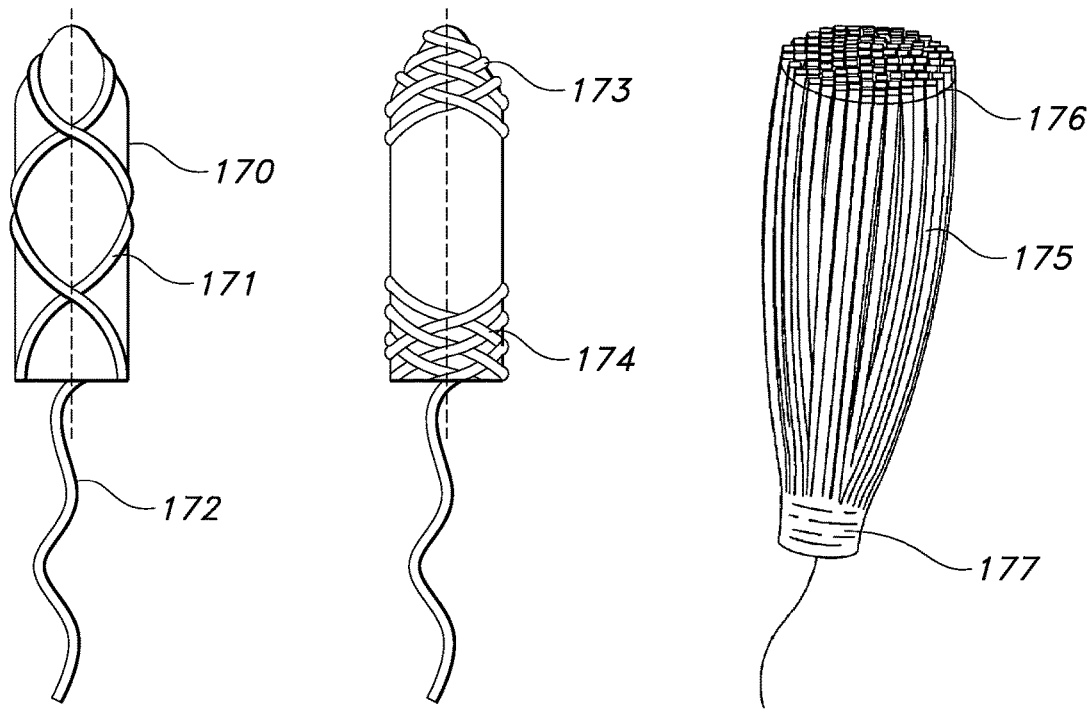
FIG. 15 is a side perspective view of an alternative embodiment of the invention in the form of a tampon.
FIG. 15A is a side perspective view of an alternative embodiment of the invention in the form of a tampon.
FIG. 15B is a side perspective view of an alternative embodiment of the invention in the form of a tampon.
Figure 15C:
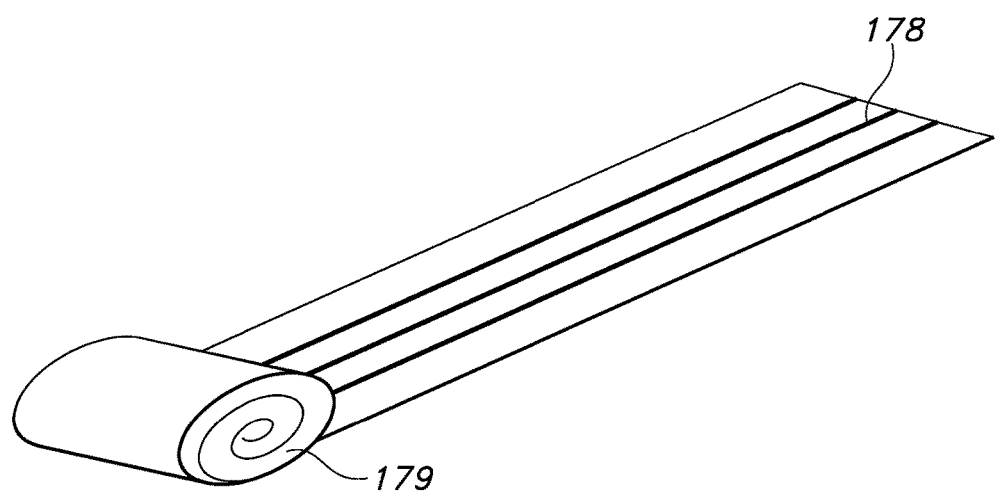
FIG. 15C is a perspective view of an absorbent pledget ribbon to be used in a tampon of the present invention, which is rolled prior to compression.

In still a further alternative embodiment of the invention, a side plan view of a feminine hygiene article, in the form of a tampon absorbent is shown in FIGS. 15, 15A and 15B. In the FIG. 15, the tampon is primarily comprised of a compressed absorbent wadding 170, around which the superabsorbent yarn 171 is wrapped. Alternatively, the superabsorbent yarn may be part of the withdrawal string 172 of the tampon. The tampon may or may not include a cover sheet over the superabsorbent yarn to assist in keeping the superabsorbent from falling from the superabsorbent yarn (depending on yarn type). In FIG. 15A, the tampon can include discrete placements of superabsorbent yarn on the tampon, such as on the upper insertion end 173 or lower withdrawal end 174 of the tampon. In such a fashion, the superabsorbent yarn can serve as a final fluid barrier to prevent leakage of menstrual fluids from the tampon either while in use, or at the time of withdrawal. As can be seen in FIG. 15B superabsorbent yarn can be formed in a tow-type fashion rather than as part of a secondary absorbent material, such that the tampon itself is comprised of numerous superabsorbent yarns 175 that are either covered or not, by a separate cover sheet 176 and which are held in place at the tampon withdrawal end by a retention element 177, such as a band, or compressed region. While the superabsorbent yarn is illustrated on the outside surface of the tampon in FIGS. 15 and 15A, it can just as easily be positioned along the inside of the tampon. For example, as seen in FIG. 15C which shows a roll of a tampon absorbent pledget ribbon that has the superabsorbent yarn 178 wrapped with the absorbent sheet of the tampon into a roll 179 prior to compression, and which would subsequently be included on the inside of the tampon absorbent following compression and tampon formation.

Figure 16:
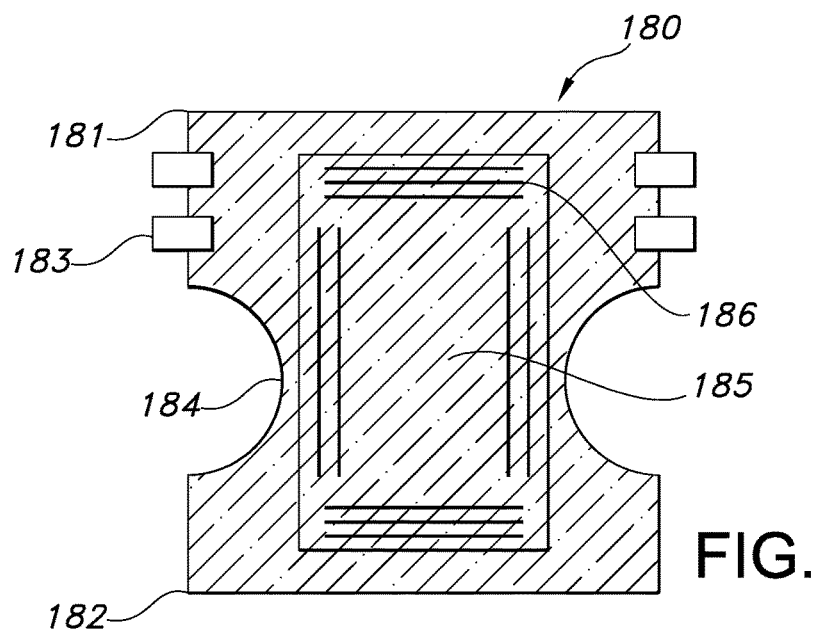
FIG. 16 is a top plan view of an alternative embodiment of the invention in the form of a diaper.
Figure 17:
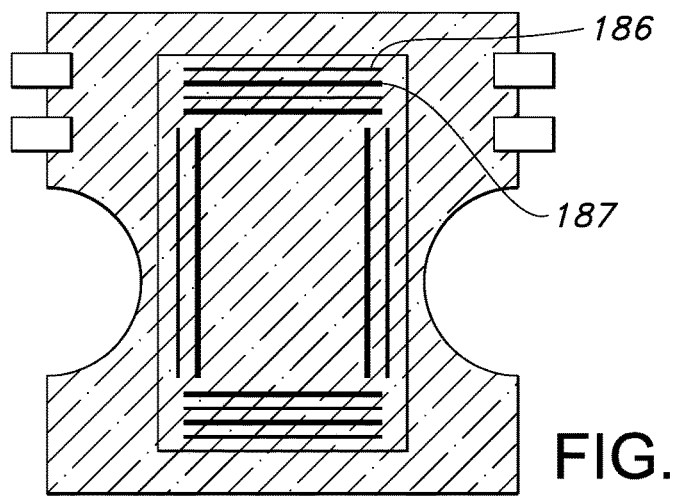
FIG. 17 is a top plan view of an alternative embodiment of the invention in the form of a diaper.
Figure 18:
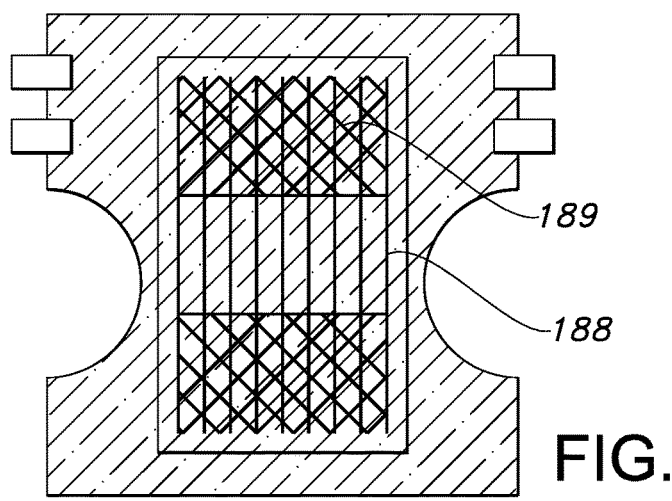
FIG. 18 is a top plan view of an alternative embodiment of the invention in the form of a diaper.
Figure 19:
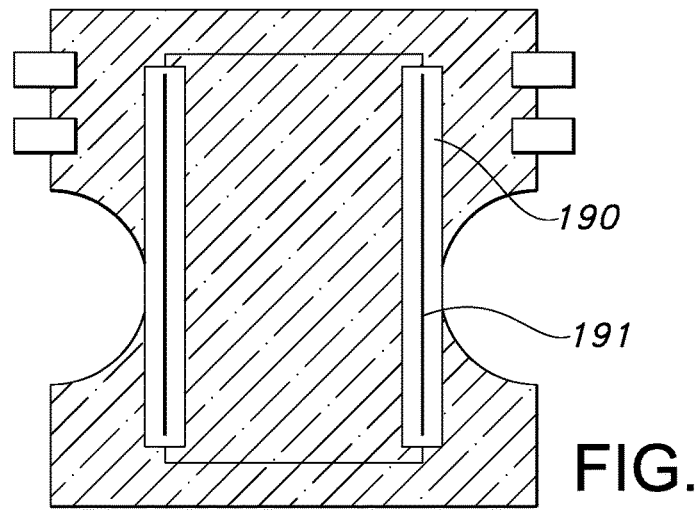
FIG. 19 is a top plan view of an alternative embodiment of the invention in the form of a diaper.
Figure 20:
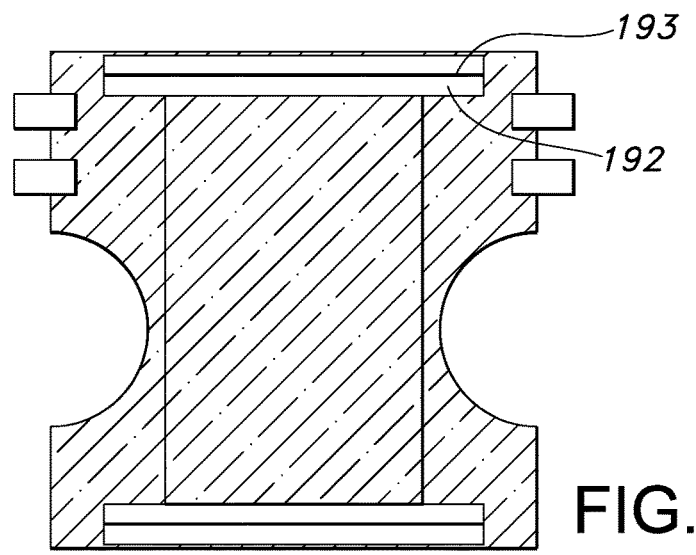
FIG. 20 is a top plan view of an alternative embodiment of the invention in the form of a diaper.
Figure 21:
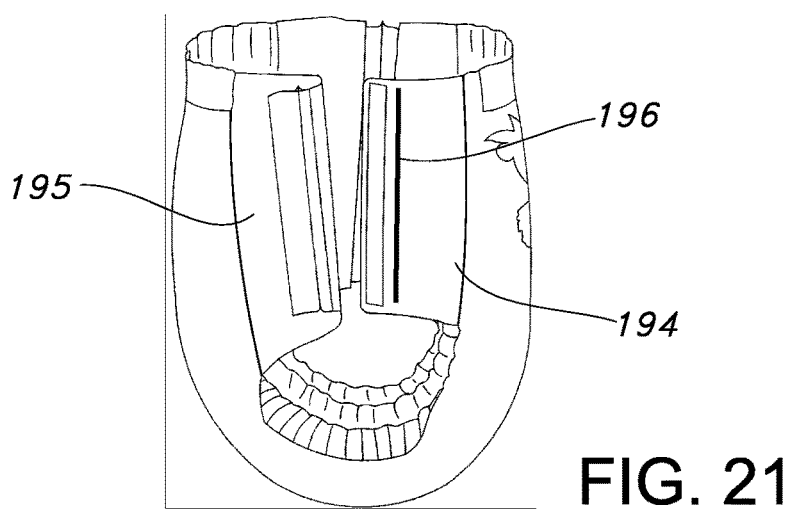
FIG. 21 is a side perspective view of an alternative embodiment of the invention in the form of a diaper.
Figure 22:
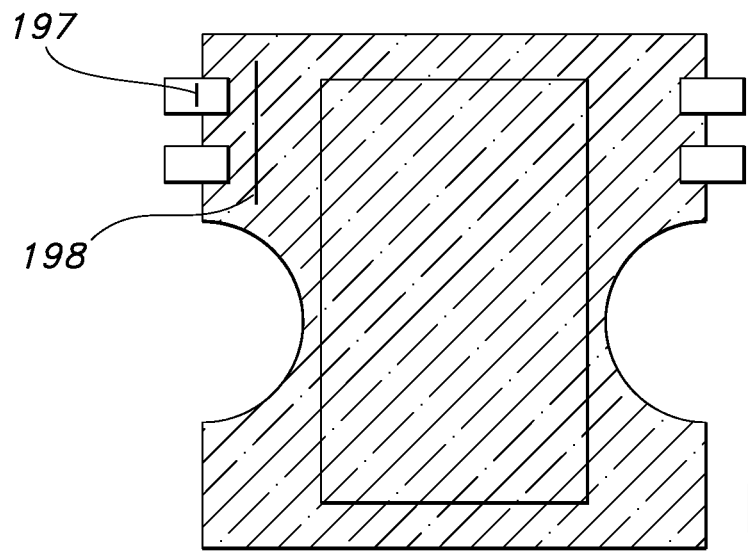
FIG. 22 is a top plan view of an alternative embodiment of the invention in the form of a diaper.

In still a further alternative embodiment of the invention, a top plan view of a diaper 180 is illustrated in FIG. 16. The diaper includes two waist regions 181 and 182 connected via a crotch region 184 and having fasteners 183 along the side edges of one waist region 181. The diaper includes a topsheet and a backsheet, which sandwich an absorbent core 185. As with the previously described feminine hygiene articles, the topsheet and backsheets can be manufactured from materials known in the art and the topsheet can in some embodiments be translucent if desired. The core can similarly be manufactured of absorbent materials known in the art. Positioned on or in the absorbent core are superabsorbent yarns 186 strategically placed along the absorbent core peripheral edges to serve as a last barrier against exudate leakage. As with the previous embodiments, the superabsorbent yarns can be affixed to a separate core layer, solely comprise the core, or affixed to a carrier sheet. As seen in FIG. 17, which illustrates an alternative diaper embodiment to that shown in FIG. 16, the absorbent core may include different functional superabsorbent yarns placed adjacent one another, 186, 187. For example, some of the superabsorbent yarns may be designed to absorb and retain relatively large amounts of exudates, while others may be designed to rapidly absorb exudates, but not retain as much. As seen in FIG. 18, which illustrates still a further alternative diaper embodiment to that shown in FIG. 16, regions of relatively high density superabsorbent yarn may be placed in the waist areas 189 to stop leakage of exudates at the waist areas, while crotch core regions between the waist areas can have directionally parallel superabsorbent yarns 188 to transport exudates to the outer regions of the absorbent core in the waist areas. As seen in FIG. 19, which illustrates still a further alternative diaper embodiment to that shown in FIG. 16, such diaper may include side flaps (or crotch area walls) 190 which traditionally include elastic components (not illustrated) in order to contain body waste in a defined area. Superabsorbent yarn 191 may be placed on or within the side flaps to serve as a final absorbent barrier to prevent exudate leakage. In a similar fashion, as can be seen in an alternative diaper embodiment in FIG. 20, the diaper may include elastic waist regions 192 which assist in diaper fit and comfort. Within the waist regions, superabsorbent yarn 193 can be placed to serve as an exudate leakage barrier. In a similar fashion, as can be seen in an alternative diaper embodiment in FIG. 21 shown in side view, the diaper may include elastic detachable side portions 194 and 195 which also assist in diaper fit and comfort. Within the side portions, superabsorbent yarn 196 can be placed to serve as an exudate leakage barrier. Finally, in a similar fashion, as can be seen in an alternative diaper embodiment in FIG. 22, the diaper may include supplemental absorbent barriers in other peripheral locations, such as on or in the fastener systems 197 or in the waist regions adjacent the fasteners 198.

Figure 23:
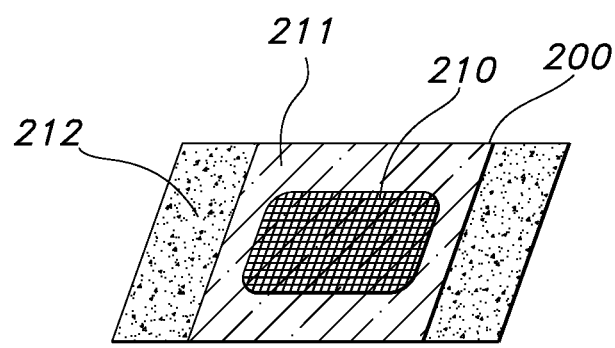
FIG. 23 is a top perspective view of an alternative embodiment of the invention in the form of a bandage.

In still a further alternative embodiment of the invention, as can be seen in the perspective view of FIG. 23, the superabsorbent yarn can be placed on a bandage substrate 200 along the central region, in the form of a matrix 210. Such matrix can be bonded to the substrate utilizing known bonding methods. Desirably the substrate 200 is of a liquid impermeable material, such as a single or multi-layered film, or nonwoven laminate, as are also known. The bandage may or may not include a fluid permeable cover layer 211. Such bandage may be capable of being wrapped around a body part, or adhesively attached to a body part via either separately attached adhesive tape or topically applied adhesive 212 on the surface of the substrate.

In other alternative embodiments, as are illustrated in FIGS. 24 and 25, the superabsorbent yarn 250 can be placed in an absorbent article in severed pieces, such as are illustrated in the figure. Such yarn pieces can provide additional surface area for absorption and allow for exudates to be absorbed also from numerous yarn ends as desired.

In an embodiment illustrated in FIG. 26, the superabsorbent yarn can be placed as a matrix upon, or within an absorbent towel substrate 260, to both provide resiliency and wet strength to the towel substrate. By providing the yarn in a transversely and longitudinally directed matrix 261, the absorbed fluids can be directed to many areas of the towel, for more efficient usage of the entire towel. As previously described, the superabsorbent yarn can be designed to absorb and retain different fluids depending on the ultimate absorbency objectives of the towel.

Not being bound to theory, it is surmised that the helical and twisting nature of superabsorbent yarns, and in particular encapsulated yarns, influences the absorbency and wicking properties of the yarns to achieve the desired absorbency characteristics in the consumer products described herein. In addition to the choices of materials in the yarn, such as the choices of filaments for internal and external layers, the variations of twist densities and directions of twists between layers making up the yarn macrostructure (as opposed to individual fiber structure making up the yarn) will influence the yarn's ability to move fluid along the yarn length and into the core regions (if distinct cores are present). It has been found that the yarn's helical structure generates local helical fluid movement along the dimensions of the absorbent article. While previously utilized linear fluid channels provide limited volume of fluid movement, helical channels may provide a balance between linear speed and increased volume of fluid movement, especially when combined with the retention properties of superabsorbent components. Fluid is traveling both radially into SAP components of the yarn, and helically along channels created around twisted filament or fibers. As fluid reaches the SAP components, the SAP expands, causing changes in fluid pathways, altering the void volumes at areas of insult.

Those skilled in the art will recognize that the present invention is capable of many modification and variations without departing from the scope thereof. Accordingly, the detailed description is meant to be illustrative only and is not intended to limit, in any manner, the scope of the invention as set forth in the appended claims.

What is claimed is:

1. An absorbent article having a longitudinal and transverse direction, and comprising a fluid permeable topsheet having an inside surface, a fluid impermeable backsheet having an inside surface, an absorbent portion positioned between said topsheet and said backsheet, characterized in that said absorbent portion is comprised of at least free strand superabsorbent yarn affixed to a carrier sheet, which carrier sheet is adjacent said fluid impermeable backsheet and bonded either to said topsheet inside surface or said backsheet inside surface, said free strand superabsorbent yarn including superabsorbent and fluid permeable components said fluid permeable components for either distributing fluid within said yarn length or alternatively for retaining fluid, wherein said free strand superabsorbent yarn is encapsulated superabsorbent yarn.

2. The absorbent article of claim 1, wherein said free strand super absorbent yarn is a multi-layered encapsulated superabsorbent yarn.

3. The absorbent article of claim 1, wherein said absorbent portion further comprises an additional absorbent layer.

4. The absorbent article of claim 1, wherein said article further includes a shaping layer.

5. The absorbent article of claim 1, wherein said article includes an additional layer between said topsheet and said absorbent portion.

6. The absorbent article of claim 5, wherein said additional layer defines one or more openings through which said free strand superabsorbent yarn is visible through said topsheet.

7. The absorbent article of claim 1, wherein said topsheet is translucent to allow the viewing of said free strand superabsorbent yarn through said topsheet.

8. The absorbent article of claim 1, wherein said absorbent article is selected from the group consisting of a feminine hygiene article, an adult incontinence article, a baby or child care article, a bandage, and a wiping towel.

9. The absorbent article of claim 8, wherein superabsorbent yarn is arranged on said article in a location separate from said absorbent portion.

10. The absorbent article of claim 8, wherein said free strand superabsorbent yarn is severed into multiple pieces along at least one direction of said article.

11. The absorbent article of claim 1, wherein said article includes peripheral edges and further, wherein said free strand superabsorbent yarn is arranged along the article's peripheral edges.

12. The absorbent article of claim 1, wherein said free strand superabsorbent yarn is arranged adjacent other strand materials.

13. The absorbent article of claim 1, wherein said free strand superabsorbent yarn is arranged such that said absorbent portion includes different strand densities of free strand superabsorbent yarn per unit area, along said absorbent portion.

* * * * *